(12) United States Patent
Sakai

(10) Patent No.: US 8,398,542 B2
(45) Date of Patent: Mar. 19, 2013

(54) LIVING BODY OBSERVATION SYSTEM AND METHOD OF DRIVING LIVING BODY OBSERVATION SYSTEM

(75) Inventor: Youhei Sakai, Ina (JP)

(73) Assignee: Olympus Corporation, Tokyo (JP)

( * ) Notice: Subject to any disclaimer, the term of this patent is extended or adjusted under 35 U.S.C. 154(b) by 219 days.

(21) Appl. No.: 12/428,639

(22) Filed: Apr. 23, 2009

(65) Prior Publication Data
US 2009/0275801 A1 Nov. 5, 2009

(30) Foreign Application Priority Data
May 1, 2008 (JP) .................... 2008-119892

(51) Int. Cl.
*A61B 1/04* (2006.01)
*A61B 1/00* (2006.01)
*A61B 5/05* (2006.01)
*A61B 19/00* (2006.01)
*A61N 2/00* (2006.01)

(52) U.S. Cl. .......... 600/118; 600/12; 600/407; 600/117; 128/899

(58) Field of Classification Search ............... 600/101, 600/110, 117, 118, 348, 109, 114, 175; 340/782; 324/207.11; 348/77
See application file for complete search history.

(56) References Cited

U.S. PATENT DOCUMENTS

| | | | | |
|---|---|---|---|---|
| 4,395,259 | A * | 7/1983 | Prestele et al. | 604/67 |
| 5,202,675 | A * | 4/1993 | Tokimoto et al. | 345/31 |
| 7,144,366 | B2 * | 12/2006 | Takizawa et al. | 600/117 |
| 2005/0043634 | A1 | 2/2005 | Yokoi et al. | |
| 2005/0054897 | A1 * | 3/2005 | Hashimoto et al. | 600/118 |
| 2005/0183733 | A1 * | 8/2005 | Kawano et al. | 128/899 |
| 2007/0032697 | A1 * | 2/2007 | Shimizu et al. | 600/101 |
| 2007/0106175 | A1 | 5/2007 | Uchiyama et al. | |
| 2007/0179576 | A1 | 8/2007 | Nagano et al. | |
| 2007/0191671 | A1 * | 8/2007 | Kawano et al. | 600/12 |
| 2007/0250126 | A1 | 10/2007 | Maile et al. | |

(Continued)

FOREIGN PATENT DOCUMENTS

| | | |
|---|---|---|
| EP | 1 637 063 A1 | 3/2006 |
| EP | 1 815 781 | 8/2007 |

(Continued)

OTHER PUBLICATIONS

European Search Report dated Jan. 4, 2013 in corresponding European Patent Application No. EP 09 73 8670.0.

*Primary Examiner* — John P Leubecker
*Assistant Examiner* — Ronald D Colque
(74) *Attorney, Agent, or Firm* — Scully Scott Murphy & Presser, PC

(57) ABSTRACT

A living body observation system of the invention includes a living body information acquiring apparatus including: a living body information acquiring section; a wireless transmission section; a power source section for supplying driving power for driving the living body information acquiring section and the wireless transmission section; a magnetic field detecting section for outputting a detection result of a magnetic field from outside as an electric signal; and a power supply control section for controlling a supplying state of the driving power based on the electric signal, a magnetic field generating coil, a driving circuit for outputting a drive signal to the magnetic field generating coil, a switch for switching a generation state of a magnetic field, and a timer for outputting a signal for stopping output of the drive signal when a predetermined period has passed following switching from off to on of the switch.

2 Claims, 2 Drawing Sheets

U.S. PATENT DOCUMENTS

| | | |
|---|---|---|
| 2007/0252441 A1 | 11/2007 | Yamauchi et al. |
| 2007/0299301 A1* | 12/2007 | Uchiyama et al. ............ 600/101 |
| 2008/0033257 A1* | 2/2008 | Yokoi et al. .................... 600/300 |
| 2008/0084478 A1* | 4/2008 | Gilad et al. .............. 348/207.99 |

FOREIGN PATENT DOCUMENTS

| | | |
|---|---|---|
| EP | 1 839 562 A1 | 10/2007 |
| EP | 1 932 463 A1 | 6/2008 |
| EP | 932 463 A1 | 6/2008 |
| EP | 1 982 635 A1 | 10/2008 |
| JP | 05-027839 A | 2/1993 |
| JP | 2001-224553 | 8/2001 |
| JP | 2004-159456 | 6/2004 |
| JP | 2005-81005 | 3/2005 |
| JP | 2005-210801 | 8/2005 |
| JP | 2005-237460 | 9/2005 |
| JP | 2005-270462 | 10/2005 |
| JP | 2005-287150 | 10/2005 |
| JP | 2005-312236 A | 11/2005 |
| JP | 2005-342083 | 12/2005 |
| JP | 2008-36243 | 2/2008 |
| JP | 2008-79913 | 4/2008 |
| WO | WO 2004/112592 A1 | 12/2004 |
| WO | WO 2005/092189 A1 | 10/2005 |
| WO | WO 2005/093927 A1 | 10/2005 |
| WO | WO 2005/102452 A1 | 11/2005 |
| WO | WO 2005/117682 A1 | 12/2005 |
| WO | WO 2006/022365 A1 | 3/2006 |
| WO | WO 2007/043458 A1 | 4/2007 |
| WO | WO 2007/083708 A1 | 7/2007 |
| WO | WO 2008/038753 A1 | 4/2008 |

* cited by examiner

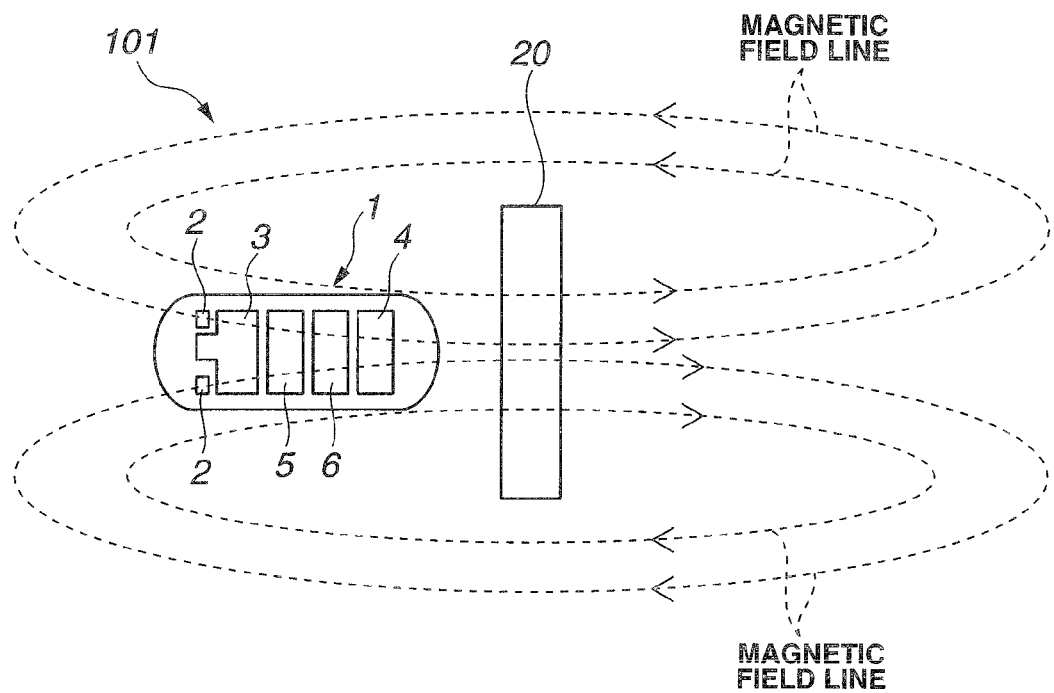
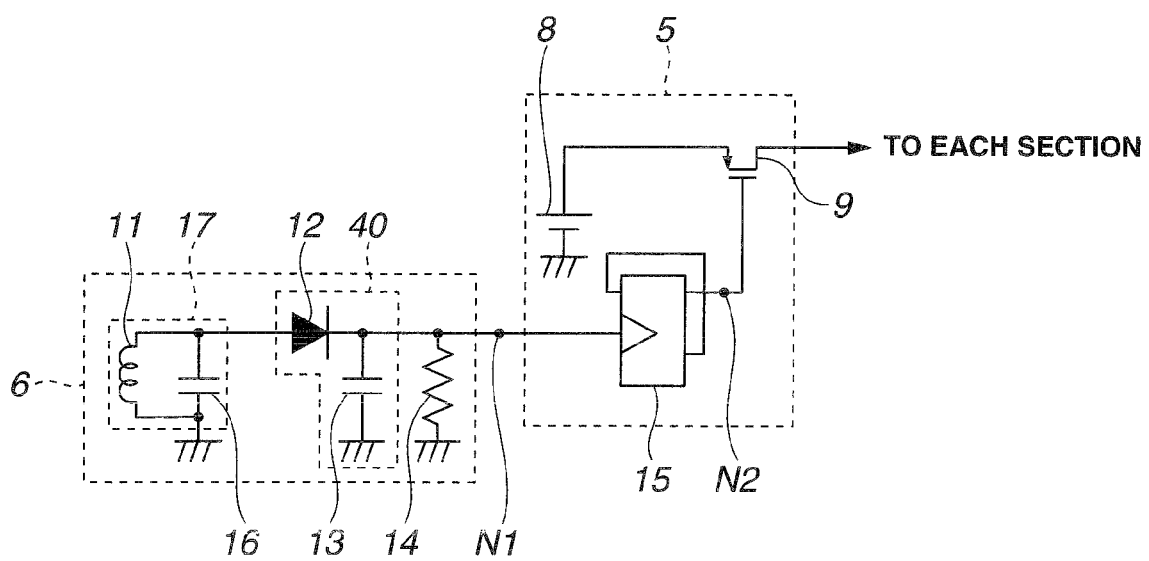

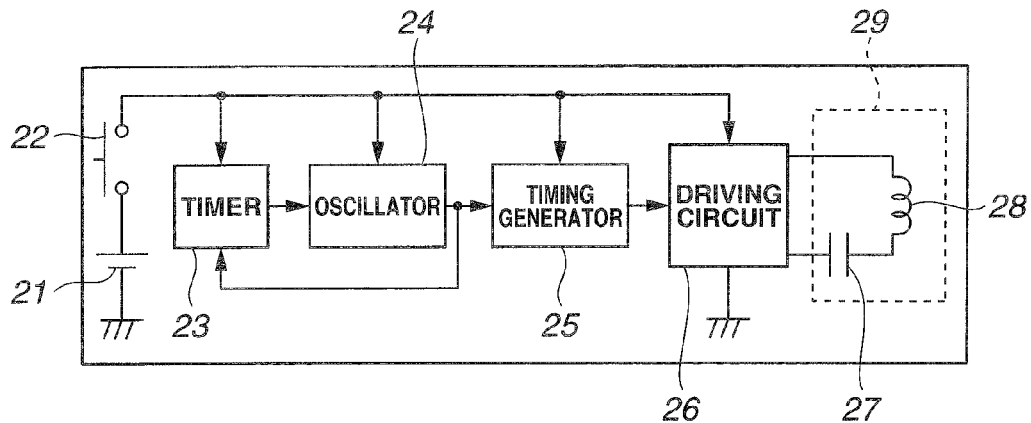
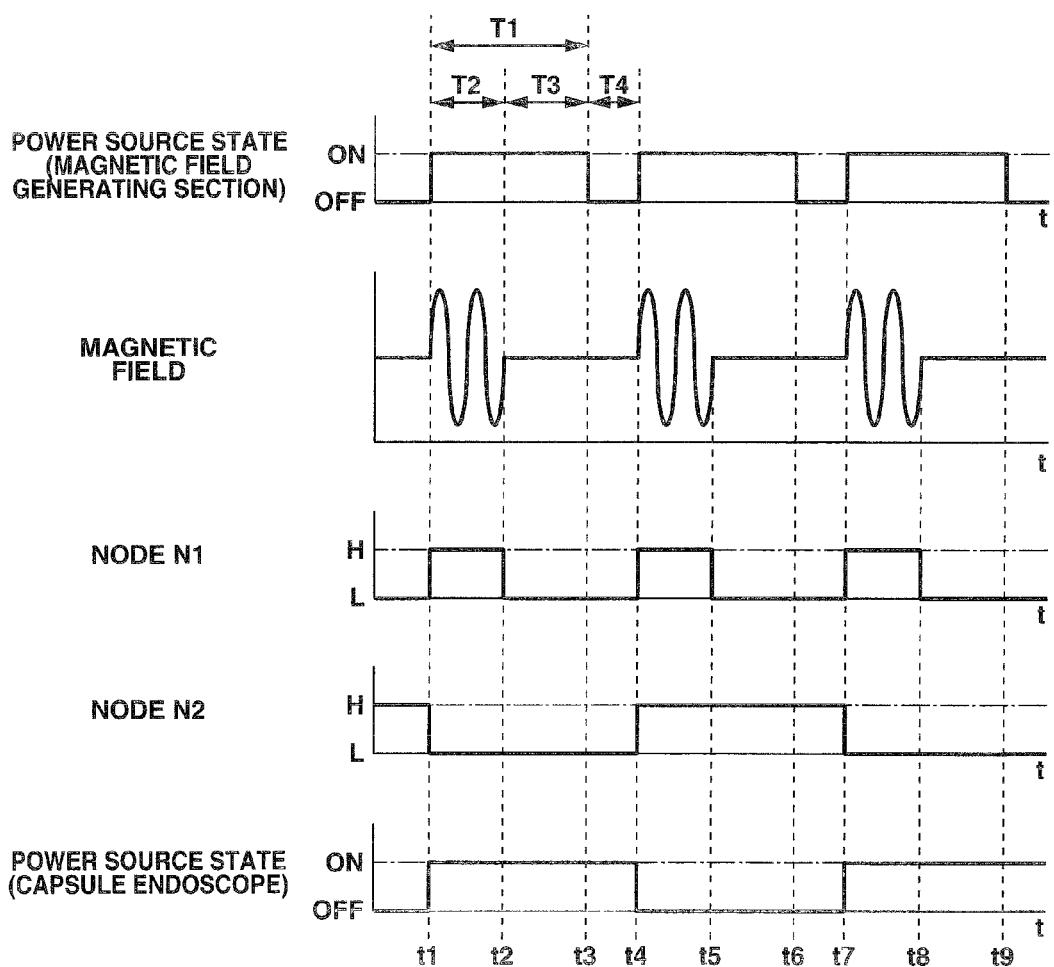

LIVING BODY OBSERVATION SYSTEM AND METHOD OF DRIVING LIVING BODY OBSERVATION SYSTEM

CROSS REFERENCE TO RELATED APPLICATION

This application claims benefit of Japanese Application No. 2008-119892 filed in Japan on May 1, 2008, the contents of which are incorporated by this reference.

BACKGROUND OF THE INVENTION

1. Field of the Invention

The present invention relates to a living body observation system and a method of driving the living body observation system, and more particularly to a living body observation system including a power source section composed of a battery or the like and a method of driving the living body observation system.

2. Description of Related Art

Conventionally, endoscopes have been widely used in the medical field or the like. Endoscopes in the medical field, in particular, are used for the purpose of observing inside of a living body. One type of the endoscopes described above is a capsule endoscope developed in recent years, which is swallowed by a test subject to be disposed in a body cavity, and capable of picking up images of a photographic subject while moving in the body cavity with peristaltic movement and wirelessly transmitting the picked-up images of the photographic subject to outside as image pickup signals.

For example, Japanese Patent Application Laid-Open Publication No. 2001-224553 discloses an apparatus having substantially the same functions as those of the capsule endoscope described above.

The Japanese Patent Application Laid-Open Publication No. 2001-224553 describes a capsule endoscope having a configuration in which a reed switch with contacts that open when placed in a magnetic field is used as a non-contact power source switch. The capsule endoscope described in the Japanese Patent Application Laid-Open Publication No. 2001-224553 is configured such that, due to the working of the above-described reed switch, the contacts of the reed switch open to turn off the power source of the endoscope when the endoscope is stored in a container or a storage case having a magnet, and the contacts close to turn on the power source (power is supplied from a battery) of the endoscope when the endoscope is taken out of the container or the storage case, for example.

SUMMARY OF THE INVENTION

The present invention provides a living body observation system which includes a living body information acquiring apparatus including: a living body information acquiring section for acquiring living body information in a living body; a wireless transmission section for wirelessly transmitting the living body information to outside of the living body; a power source section for supplying driving power for driving the living body information acquiring section and the wireless transmission section; a magnetic field detecting section for detecting a magnetic field from outside and outputting a detection result as an electric signal; and a power supply control section for controlling a supplying state of the driving power supplied from the power source section to the living body information acquiring section and the wireless transmission section based on the electric signal, and which also includes a magnetic field generating section disposed outside the living body information acquiring apparatus, the magnetic field generating section including: a magnetic field generating coil; a driving circuit for outputting a drive signal for driving the magnetic field generating coil; a switch for switching between on and off of a generation state of a magnetic field in the magnetic field generating coil; and a timer for outputting a stop signal for stopping output of the drive signal when a predetermined period has passed following switching from off to on of the switch.

The present invention also provides a method of driving the living body observation system which includes a living body information acquiring apparatus including: a living body information acquiring section for acquiring living body information in a living body; a wireless transmission section for wirelessly transmitting the living body information to outside of the living body; a power source section for supplying driving power for driving the living body information acquiring section and the wireless transmission section; a magnetic field detecting section for detecting a magnetic field from outside and outputting a detection result as an electric signal; and a power supply control section for controlling a supplying state of the driving power supplied from the power source section to the living body information acquiring section and the wireless transmission section based on the electric signal, and which also includes a magnetic field generating section disposed outside the living body information acquiring apparatus, the magnetic field generating section including: a magnetic field generating coil; a driving circuit for outputting a drive signal for driving the magnetic field generating coil; a switch for switching between on and off of a generation state of a magnetic field in the magnetic field generating coil; and a timer for outputting a stop signal for stopping output of the drive signal when a predetermined period has passed following switching from off to on of the switch. The method includes switching a power source state of the living body information acquiring apparatus between on and off every time the magnetic field is generated from the magnetic field generating section.

BRIEF DESCRIPTION OF THE DRAWINGS

FIG. 1 is a view showing a configuration of a main part of a living body observation system according to an embodiment of the present invention.

FIG. 2 is a view showing an example of a specific configuration of a power supplying section and a magnetic field detecting section according to the embodiment of the present invention.

FIG. 3 is a view showing an example of a specific configuration of a magnetic field generating section according to the embodiment of the present invention.

FIG. 4 is a timing chart showing operating states of the magnetic field generating section and a capsule endoscope according to the embodiment of the present invention.

DETAILED DESCRIPTION OF THE PREFERRED EMBODIMENT

Hereinafter, an embodiment of the present invention will be described with reference to the drawings.

FIGS. 1 to 4 relate to the embodiment of the present invention. FIG. 1 is a view showing a configuration of a main part of a living body observation system according to an embodiment of the present invention. FIG. 2 is a view showing an example of a specific configuration of a power supplying section and a magnetic field detecting section according to the embodiment of the present invention. FIG. 3 is a view showing an example of a specific configuration of a magnetic field generating section according to the embodiment of the present invention. FIG. 4 is a timing chart showing operating states of the magnetic field generating section and a capsule endoscope according to the embodiment of the present invention.

As shown in FIG. 1, a living body observation system 101 includes a capsule endoscope 1 having a size and a shape which can be disposed in a living body, and a magnetic field generating section 20 that generates a magnetic field outside the capsule endoscope 1.

As shown in FIG. 1, the capsule endoscope 1 includes inside thereof: an illuminating section 2 for emitting illumination light for illuminating a photographic subject in a living body; an image pickup section 3 for picking up an image of the photographic subject illuminated by the illuminating section 2 and outputting the picked-up image as an image pickup signal; a wireless transmission section 4 for wirelessly transmitting the image pickup signal outputted from the image pickup section 3 to outside of the living body; a power supplying section 5 for supplying driving power required for driving each of the illuminating section 2, the image pickup section 3 and the wireless transmission section 4; and a magnetic field detecting section 6 capable of detecting the magnetic field generated by the magnetic field generating section 20.

That is, a living body information acquiring section of the present embodiment is configured by including the illuminating section 2 and the image pickup section 3.

On the other hand, the power supplying section 5 is configured by including a power source section 8 composed of a battery or the like, a P-channel FET 9, and a frequency divider circuit 15 for dividing an output signal from the magnetic field detecting section 6 by two, as shown in FIG. 2.

The P-channel FET 9 has the source connected to the power source section 8, the gate connected to an output end of the frequency divider circuit 15, and the drain connected to each of the illuminating section 2, the image pickup section 3, and the wireless transmission section 4.

Note that the power supplying section 5 is not limited to one configured by using the P-channel FET 9 and may be one configured by using an electronic switch or the like having a similar switching function as that of the P-channel FET 9.

As shown in FIG. 2, the magnetic field detecting section 6 is configured by including a magnetic field receiving antenna 17 for outputting an electric signal corresponding to a magnetic field generated by the magnetic field generating section 20, and a rectifying section 40 for rectifying the electric signal outputted from the magnetic field receiving antenna 17 and outputting the rectified electric signal, and a resistor 14.

The magnetic field receiving antenna 17 is configured as a resonant circuit that includes: a magnetic field detecting coil 11 for outputting an electric signal corresponding to the magnetic field generated by the magnetic field generating section 20; and a resonant capacitor 16 connected to an input end of a diode 12 in parallel with the magnetic field detecting coil 11. Note that the resonant circuit including the magnetic field detecting coil 11 and the resonant capacitor 16 is configured such that the resonant frequency of the resonant circuit itself agrees with the frequency of the magnetic field generated by the magnetic field generating section 20.

Note that the magnetic field receiving antenna 17 is not limited to one configured as the parallel resonant circuit which includes the magnetic field detecting coil 11 and the resonant capacitor 16. The magnetic field receiving antenna 17 may be configured as a series resonant circuit in which the magnetic field detecting coil 11 and the resonant capacitor 16 are connected in series.

In addition, the magnetic field detecting coil 11 may be formed of, for example, a solenoid coil or a planar coil, and may have any shape as long as the magnetic field detecting coil 11 can be disposed in the capsule endoscope 1.

The rectifying section 40 has the diode 12, an input end of which is connected to an output end of the magnetic field detecting coil 11, and a smoothing capacitor 13 for smoothing an electric signal outputted from the diode 12. Note that the rectifying section 40 of the present embodiment is not limited to one for performing half-wave rectification, and may be one for performing full-wave rectification.

The resistor 14 is connected to an output end of the diode 12 in parallel with the smoothing capacitor 13.

As shown in FIG. 3, the magnetic field generating section 20 is configured by including: a power source section 21 composed of a battery, a stabilized power source, a built-in battery, or the like; a switch 22 capable of switching a supplying state of power from the power source section 21 between on and off; a timer 23; an oscillator 24; a timing generator 25; a driving circuit 26; and a magnetic field transmitting antenna 29. The magnetic field transmitting antenna 29 is configured as a resonant circuit which includes: a magnetic field generating coil 28 for generating a magnetic field corresponding to a drive signal outputted from the driving circuit 26; and a resonant capacitor 27 connected to an output end of the driving circuit 26 in series with the magnetic field generating coil 28.

Note that the magnetic field transmitting antenna 29 is not limited to one configured as the parallel resonant circuit including the magnetic field generating coil 28 and the resonant capacitor 27. The magnetic field transmitting antenna 29 may be configured as a series resonant circuit in which the magnetic field generating coil 28 and the resonant capacitor 27 are connected in series or as a non-resonant circuit to which the resonant capacitor 27 is not connected.

Furthermore, the switch 22 of the present embodiment is not limited to one disposed at the position (the power supply line of the power source section 21) shown in FIG. 3, as long as the switch is disposed at a position capable of switching the generation state of the magnetic field in the magnetic field generating section 20 between on and off.

The magnetic field generating coil 28 may be formed of a solenoid coil or a planar coil, for example, and may have any shape as long as the magnetic field generating coil 28 can be disposed in the magnetic field generating section 20.

The timer 23 is configured of a counter, a timing circuit, or the like and starts counting time at the timing when an oscillating signal is inputted from the oscillator 24. In addition, the timer 23 outputs a stop signal for stopping the oscillating signal from the oscillator 24 at the timing when a predetermined period set in advance has passed following the start of time counting.

The oscillator 24 starts oscillating at the timing immediately after the switch 22 was turned on, and outputs an oscillating signal to the timer 23 and the timing generator 25. In addition, the oscillator 24 stops outputting the oscillating signal at the timing when the stop signal is inputted from the timer 23.

The timing generator 25 is configured of a frequency divider circuit or the like, for example. The timing generator 25 performs signal processing for changing the frequency of the oscillating signal from the oscillator 24 to a predetermined frequency and outputs the signal-processed oscillating signal to the driving circuit 26 as a timing signal.

The driving circuit 26 outputs voltage for driving the magnetic field generating coil 28 as a drive signal in the period during which the timing signal is inputted to the driving circuit 26 from the timing generator 25.

Note that the timer 23 of the present embodiment is not limited to one for outputting to the oscillator 24 the stop signal for stopping the output of the oscillating signal. The timer 23 may be one for outputting to the timing generator 25 the stop signal for stopping the output of the timing signal, or one for outputting to the driving circuit 26 the stop signal for stopping the output of the drive signal, for example.

Now, a working of the living body observation system 101 of the present embodiment will be described.

First, an operator or the like takes out the capsule endoscope 1 from a case, not shown, in which the endoscope is stored. Then, the operator or the like applies a magnetic field to the capsule endoscope 1 by switching the switch 22 of the magnetic field generating section 20 from off to on.

Note that the application of the magnetic field from the magnetic field generating section 20 is not limited to be performed after the capsule endoscope 1 was taken out from the case not shown, but may be performed while the capsule endoscope 1 is stored in the case.

As shown in FIG. 4, when the switch 22 of the magnetic field generating section 20 is switched from off to on at the time t1, power is supplied from the power source section 21 to each of the timer 23, the oscillator 24, the timing generator 25, and the driving circuit 26.

When the switch 22 is turned on at the time t1 shown in FIG. 4, the oscillator 24 starts output of the oscillating signal, the timer 23 starts time counting accompanying the input of the oscillating signal, the timing generator 25 starts output of the timing signal accompanying the input of the oscillating signal, and the driving circuit 26 starts output of the drive signal accompanying the input of the timing signal. As a result, the magnetic field generating coil 28 starts generating a magnetic field at the time t1 shown in FIG. 4.

When the timer 23 detects that the time t2 shown in FIG. 4 has passed, for example, based on the time counting started at the time t1, the timer 23 outputs to the oscillator 24 a stop signal for stopping the output of the oscillating signal. When the output of the oscillating signal from the oscillator 24 is stopped, the output of the timing signal accompanying the input of the oscillating signal is stopped, the output of the drive signal accompanying the input of the timing signal is stopped, and the generation of the magnetic field accompanying the input of the drive signal is stopped.

That is, among the period T1 from the time t1 to the time t3 as the period during which the switch 22 continues to be turned on, the magnetic field generating section 20 generates a magnetic field during the period T2 from the time t1 to the time t2, and stops generating the magnetic field during the period from the time t2 to the time t3, as shown in FIG. 4.

However, the above-described period T2 is a fixed period set in advance in the timer 23 as the predetermined period. As a result, the magnetic field generating section 20 of the present embodiment continues to generate a magnetic field during the period T2, irrespective of the length of the period T1 as the period during which the switch 22 continues to be turned on. Specifically, the magnetic field generating section 20 of the present embodiment continues to generate a magnetic field during the period T2, even when the switch 22 is turned on by a trigger-like signal, that is, the period T1 during which the switch 22 is turned on is extremely short.

Also after the time t4, each component of the magnetic field generating section 20 repeatedly performs the above described operations related to the generation and stop of the magnetic field in accordance with the on/off switching of the switch 22.

When the magnetic field generating section 20 starts generating the magnetic field at the time t1, an electric potential difference is generated between both ends of the magnetic field detecting coil 11 by electromagnetic induction, and thereafter alternating-current electric signal corresponding to the electric potential difference is outputted to the rectifying section 40.

The alternating-current electric signal outputted from the magnetic field detecting coil 11 is then rectified in the rectifying section 40 and thereby converted into a direct-current electric signal and outputted to an input end of the frequency divider circuit 15. As a result, the electric potential level of the node N1 is shifted from a low (hereinafter referred to as L) level to a high (hereinafter referred to as H) level at the timing of the time t1, as shown in FIG. 4.

After that, when the magnetic field generating section 20 stops generating the magnetic field at timing of time t2, an electric charge accumulated in the smoothing capacitor 13 is discharged via the resistor 14. With this electric discharge, the electric potential level of the node N1 is shifted from the H level to the L level, as shown in FIG. 4.

That is, the electric potential level of the node N1 on the output end side of the magnetic field detecting section 6 of the present embodiment becomes H level in the period T2 during which the magnetic field is generated from the magnetic field generating section 20, and becomes L level in the periods T3 and T4 during which the magnetic field is not generated from the magnetic field generating section 20.

Furthermore, an output signal having the electric potential level of the node N1 is inputted to the input end of the frequency divider circuit 15. In response to this, the electric potential level of the node N2 on the output end side of the frequency divider circuit 15 is shifted from the H level to the L level at the time t1.

Following the shift of the electric potential level of the node N2 from the H level to the L level, the P-channel FET 9 is shifted from the off-state to the on-state, and thereby the power source section 8 starts supplying the driving power to each of the illuminating section 2, the image pickup section 3, and the wireless transmission section 4. That is, as shown in FIG. 4, the power source of the capsule endoscope 1 is turned on at the time t1 when the switch 22 of the magnetic field generating section 20 was turned on.

As shown in FIG. 4, the electric potential level of the node N2 is maintained at the L level, even when the electric potential level at the node N1 is shifted from the H level to the L level. Accordingly, the electric potential level of the node N2 remains at the L level until the time t4 which is the timing when the electric potential level of the node N1 is shifted again from the L level to the H level. As a result, the capsule endoscope 1 maintains the on-state during the period from the time t1 to the time t4, as shown in FIG. 4.

Furthermore, as shown in FIG. 4, the electric potential level of the node N2 is shifted from the L level to the H level at the time t4. Following the level shift, the P-channel FET 9 is shifted from the on-state to the off-state, and thereby the power source section 8 stops the supply of the driving power to each of the illuminating section 2, the image pickup section 3, and the wireless transmission section 4.

As shown in FIG. 4, after having been turned off at the time t4, the capsule endoscope 1 maintains the off-state until the time t7 when the electric potential of the node N1 is shifted again from the L level to the H level by applying the magnetic field from the magnetic field generating section 20.

That is, the capsule endoscope 1 of the present embodiment has a configuration and working such that on/off switching of the power source is performed every time the generation state of the magnetic field in the magnetic field generating section 20 is switched from off to on.

Accordingly, the living body observation system 101 of the present embodiment enables easy on/off switching of the power source of the capsule endoscope 1 at a user's desired timing, thereby enabling easier control of exhaustion of the power source section 8 of the capsule endoscope 1 compared with a conventional system.

The user turns on the capsule endoscope 1 by applying the magnetic field generated from the magnetic field generating section 20, and disposes the capsule endoscope 1 in a body of a person to be inspected by making the person to swallow the capsule endoscope 1, and thereafter starts the observation in the body.

After starting the observation in the body of the person to be inspected, the user may keep the on-state of the capsule endoscope 1, or may arbitrarily switch between on and off of the power source of the capsule endoscope 1 disposed in the body of the person to be inspected by the application of the magnetic field generated from the magnetic field generating section 20. Specifically, the user may perform observation using a method of turning off the power source of the capsule endoscope 1 in the period during which the capsule endoscope is passing through a region where observation is unnecessary, and turning on the power source of the capsule endoscope 1 by applying the magnetic field from the magnetic field generating section 20 when the capsule endoscope 1 has reached a desired region, for example. The living body observation system 101 of the present embodiment which has the configuration and working capable of carrying out such a method improves the accuracy of the observation and diagnosis in the user's desired region.

In addition, the living body observation system 101 of the present embodiment is configured such that the frequency of the magnetic field generated from the magnetic field generating section 20 agrees with the resonant frequency fr2 of the resonant circuit composed of the magnetic field detecting coil 11 and the resonant capacitor 16. Accordingly, the living body observation system 101 of the present embodiment enables the magnetic field detecting section 6 to have improved detection sensitivity to the magnetic field generated from the magnetic field generating section 20 and reduced detection sensitivity to an unintended disturbance magnetic field. As a result, the living body observation system 101 of the present embodiment can stably and surely perform the on/off switching of the power source of the capsule endoscope 1.

Since the living body observation system 101 of the present embodiment has a configuration in which a magnetic field is generated only during the predetermined period T2 set in advance, the power consumption in the magnetic field generating section 20 can be reduced.

Note that the on/off switching of the power source of the capsule endoscope 1 can be similarly performed not only in the case where the capsule endoscope 1 is disposed in the living body but also in the case where the capsule endoscope 1 is disposed outside the living body.

In addition, the embodiment described above is not limited to one applied to the capsule endoscope, but may be one applied to various living body information acquiring apparatuses having a configuration for acquiring living body information such as a temperature, pH or the like inside a living body.

Furthermore, in the above-described embodiment, a limiter circuit for suppressing the rise in the electric potential of the node N1 may be added.

It is needless to say that the present invention is not limited to the above-mentioned embodiments, and various changes and applications can be made therein without departing from the scope of the invention.

What is claimed is:

1. A living body observation system comprising,
   a living body information acquiring apparatus including: a living body information acquiring section for acquiring living body information in a living body;
   a wireless transmission section for wirelessly transmitting the living body information to outside of the living body;
   a power source section for supplying driving power for driving the living body information acquiring section and the wireless transmission section;
   a magnetic field detecting section for detecting a magnetic field from outside and outputting a detection result as an electric signal; and
   a power supply control section for controlling a supplying state of the driving power supplied from the power source section to the living body information acquiring section and the wireless transmission section based on the electric signal; wherein
   the power supply control section controls the power source section to start supplying driving power upon the detection of the electric signal and controls the power source section to stop supplying driving power upon the detection of the electric signal;
   a magnetic field generating section disposed outside the living body information acquiring apparatus, the magnetic field generating section including:
   a power source section configured by one of a battery or built-in battery;
   a magnetic field generating coil;
   a driving circuit for outputting a drive signal for driving the magnetic field generating coil;
   a switch for witching between on and off of a generation state of an alternate-current magnetic field in the magnetic field generating coil; and
   a timer for outputting a stop signal for stopping output of the drive signal when a predetermined period has passed following switching from off to on of the switch, irrespective of whether the switch is on or off; wherein
   the magnetic field generating section is configured to start a generation of the alternate-current magnetic field when the switch is switched from off to on, and to stop the generation of the alternate-current magnetic field after a predetermined period has passed, irrespective of whether the switch is on or off.

2. The living body observation system according to claim 1, wherein the living body information acquiring apparatus is a capsule endoscope.

* * * * *